United States Patent [19]
Docherty et al.

[11] Patent Number: 5,990,293
[45] Date of Patent: Nov. 23, 1999

[54] HUMAN METALLOPROTEINASE, VARIANTS THEREOF AND DNA SEQUENCE CODING THEREFOR

[75] Inventors: Andrew James Penrose Docherty, Guilford; Patrick Marcel Slocombe, Bracknell, both of United Kingdom

[73] Assignee: Celltech Therapeutics Limited, Berkshire, United Kingdom

[21] Appl. No.: 08/836,442

[22] PCT Filed: Sep. 5, 1996

[86] PCT No.: PCT/GB96/02181

§ 371 Date: Jul. 30, 1997

§ 102(e) Date: Jul. 30, 1997

[87] PCT Pub. No.: WO97/09430

PCT Pub. Date: Mar. 13, 1997

[51] Int. Cl.$^6$ ............ C07H 21/02; C07H 21/04; C07K 14/00; C12Q 1/68
[52] U.S. Cl. ............ 536/23.1; 536/24.3; 536/23.2; 530/350; 435/6
[58] Field of Search ................ 536/23.1, 24.3, 536/23.2; 530/350; 435/6

[56] References Cited

U.S. PATENT DOCUMENTS

| | | | |
|---|---|---|---|
| 5,270,447 | 12/1993 | Liotta et al. | 530/326 |
| 5,280,106 | 1/1994 | Lioota et al. | 530/330 |
| 5,372,809 | 12/1994 | Liotta et al. | 424/185.1 |
| 5,482,848 | 1/1996 | Dickson et al. | 435/219 |
| 5,698,671 | 12/1997 | Stetler-Stevenson et al. | 530/324 |

FOREIGN PATENT DOCUMENTS

WO 95/06031  3/1995  WIPO .

OTHER PUBLICATIONS

Shapiro et al., J. Biological Chemistry 268(32) : 23,824–23, 829 (1993).
Basset et al., Nature 348 :699–740 (1990).
Takinoi et al., J. of Biological Chemistry 270(39) :23, 013–23, 020 (Sep. 1995).
Sirum et al., Biochemistry 28 :8691–8698 (1989).
Puente et al., Cancer Research 56: 944–949 (Mar. 1996).
Freije et al., Biological Chemistry 269(4) :16,766–16,773 (1994).
Will et al., Eur. of Biochemistry 231 :602–608 (1995).
McKie et al., Biochem. J. 318 : 459–462 (1996).
Levy et al., Genomics 13 :881–883 (1992).
Hite, et al., Biochem., vol. 31, 6203–6211 (1992).
Will, et al., Biochem., vol. 271, No. 29, 17119–17123 (1996).
Pei, et al., Nature, vol. 375, 244–247 (1995).
Crabbe, et al., Biochemistry 33, 14419–14425 (1994).
Murphy, et al., J. of Bio Chem., vol. 267, No. 14, 9612–9618 (1992).
Feehan, et al., . Biochem., vol. 271, No. 12, 7019–7024 (1996).
Walchek, et al., Nature, vol. 380 720–723 (1996).
Lasky, Science, vol. 258, 964–969 (1992).
Mohler, et al., Nature, vol. 370, 218–220 (1994).
Gearing, et al., Nature, vol. 370, 555–561 (1994).
Edamatsu, et al., Biochem., vol. 112, No. 5, 637–642 (1992).
McGeehan, et al., Nature, vol. 370, 558–561 (1994).

*Primary Examiner*—W. Gary Jones
*Assistant Examiner*—Ethan Whisenant
*Attorney, Agent, or Firm*—Dike, Bronstein Roberts & Cushman, LLP; Lisa Swiszcz Hazzard; David G. Conlin

[57] ABSTRACT

A human metalloproteinase is described together with nucleic acids coding therefor and corresponding antisense DNA and RNA. The metalloproteinase may be used to generate antibodies therefor and to obtain compounds capable of regulating the action of the metalloproteinase in vivo.

8 Claims, No Drawings

HUMAN METALLOPROTEINASE, VARIANTS THEREOF AND DNA SEQUENCE CODING THEREFOR

This application is a 371 of PCT/GB96/02181 filed Sep. 5, 1996.

This invention relates to a novel human metalloproteinase, to homologues and fragments thereof, to means for producing the metalloproteinase, and to means for regulating its production and activity in vivo.

A number of physiologically important processing events are mediated by metalloproteinases, which under certain circumstances may contribute to pathologies as diverse as inflammation and cancer, and it has been suggested that such enzymes would provide targets for therapeutic intervention. Thus, by varying the production of the enzyme, or inhibiting or enhancing its activity in vivo it should be possible to achieve a therapeutic effect.

In one example, tumour necrosis factor-alpha (TNF-α) is a potent pro-inflammatory and immunomodulatory mammalian cytokine produced primarily by activated monocytes and macrophages. It is initially expressed as a 233-amino-acid membrane-anchored precursor (pro-TNF-α) which is proteolytically processed to yield the mature, 157-amino-acid cytokine. Evidence has been obtained which indicates that at least one metalloproteinase-like enzyme mediates pro-TNF-α cleavage, but to date the enzyme(s) responsible for this in vivo are unknown [see for example Mohler, K M et al, Nature 370, 218–220 (1994); Gearing, A J et al 370, 555–557 (1994); McGeehan, G M et al, ibid 370, 558–561 (1994)]. A number of known matrix metalloproteinase inhibitors have been shown to block TNF-α secretion [see the above papers and International Patent Specification Publication No. WO 95/06031]. These compounds were originally designed to selectively inhibit matrix metalloproteinases such as collagenase with primary functions unrelated to pro-TNF-α cleavage. Where new inhibitors have been described these have apparently been selected on the basis of their effect on TNF-α secretion seen in cell-based assays.

In another example, L-selectin shedding is thought to be a pro-inflammatory event that is mediated by an as yet unidentified metalloproteinase [Lasky, Science, 258, 964–969 (1992)]. Some inhibitors of L-selectin proteolysis have been identified, but these have been obtained using cell based assays [Walchech et al., Nature, 380, 720–723 (1996); Feehan et al., J. Biol. Chem., 271, 7019–7024 (1996)].

In general, in order to obtain compounds capable of selectively regulating the action of a metalloproteinase implicated in human disease, for example as in the above TNF-α and L-selectin instances it would be clearly advantageous to have the enzyme unequivocally identified and obtainable in an isolated, purified and unambiguous characterised form.

Through the use of a cloning and screening approach, we have been able to identify human DNA which is responsible for coding one such metalloproteinase. This DNA has the sequence described in SEQ I.D. No: 1 below and may be of use (1) in the production of the metalloproteinase, (2) in the provision of means to regulate the activity of the metalloproteinase in vivo, and (3) in the provision of means to detect and measure a metalloproteinase in a biological system, e.g. in serum, synovial fluid or a tissue extract.

Thus according to one aspect of the invention we provide isolated human DNA comprising the nucleotide sequence of SEQ I.D. No: 1:

SEQ I.D. NO: 1

```
GAGAAGAGCAGACACCGTGCTCCTGGAATCACCCAGCATGTTGCAA
GGTCTCCTGCCAGTCAGTCTCCTCCTCTCTGTTGCAGTAAGTGCTAT
AAAAGAACTCCCTGGGGTGAAGAAGTATGAAGTGGTTTATCCTATAA
GACTTCATCCACTGCATAAAAGAGAGGCCAAAGAGCCAGAGCAACAG
GAACAATTTGAAACTGAATTAAAGTATAAAATGACAATTAATGGAAAAA
TTGCAGTGCTTTATTTGAAAAAAAACAAGAACCTCCTTGCACCAGGCT
ACACGGAAACATATTATAATTCCACTGGAAAGGAGATCACCACAAGC
CCACAAATTATGGATGATTGTTATTATCAAGGACATATTCTTAATGAAA
AGGTTTCTGACGCTAGCATCAGCACATGTAGGGGTCTAAGGGGCTAC
TTCAGTCAGGGGGATCAAAGATACTTTATTGAACCTTTAAGCCCCATA
CATCGGGATGGACAGGAGCATGCACTCTTCAAGTATAACCCTGATGA
AAAGAATTATGACAGCACCTGTGGGATGGATGGTGTGTTGTGGGCCC
ACGATTTGCAGCAGAACATTGCCCTACCTGCCACCAAACTAGTAAAAT
TGAAAGACAGGAAGGTTCAGGAACATGAGAAATACATAGAATATTATT
TGGTCCTGGATAATGGTGAGTTTAAAAGGTACAATGAGAATCAAGAT
GAGATCAGAAAGAGGGTATTTGAGATGGCTAATTATGTCAACATGCTT
TATAAAAAGCTCAATACTCATGTGGCCTTAGTTGGTATGGAAATCTGG
ACTGACAAGGATAAGATAAAGATAACCCCAAATGCAAGCTTCACCTTG
GAGAATTTTTCTAAATGGAGGGGGAGTGTTCTCTCAAGAAGAAAGCG
TCATGATATTGCTCAGTTAATCACAGCAACAGAACTTGCTGGAACGAC
TGTGGGTCTTGCATTTATGTCTACAATGTGTTCTCCTTATTCTGTTGG
CGTTGTTCAGGACCACAGCGATAATCTTCTTAGAGTTGCAGGGACAA
TGGCACATGAAATGGGCCACAACTTTGGAATGTTTCATGACGACTATT
CTTGCAAGTGTCCTTCTACAATATGTGTGATGGACAAAGCACTGAGCT
TCTATATACCCACAGACTTCAGTTCCTGCAGCCGTCTCAGCTATGACA
AGTTTTTTGAAGATAAATTATCAAATTGCCTCTTTAATGCTCCATTGCC
TACAGATATCATATCCACTCCAATTTGTGGGAACCAGTTGGTGGAAAT
GGGAGAGGACTGTGATTGTGGGACATCTGAGACATGTAAAATCAAAG
CAACTTTTCAATGTGCATTAGGAGAATGTTGTGAAAAATGCCAATTTA
AAAAGGCTGGGATGGTGTGCAGACCAGCAAAAGATGAGTGCGACCT
GCCTGAAATGTGTAATGGTAAATCTGGTAATTGTCCTGATGATAGATT
CCAAGTCAATGGCTTCCCTTGCCATCACGGGAAGGGCCACTGCTTGA
TGGGGACATGCCCCACACTGCAGGAGCAGTGCACAGAGCTGTGGGG
ACCAGGTAGGAGGACAAATCCTTTCCCCTGTGCATGTGCGAAGGAAA
ATCATTTCAGATGACAGTGTTTAACCATGGTCAAAGGACCATTCTGTC
CTATCCTTCTTAGAAGCTTCGAACTCAAAATCATGGAAAGGTTTTAAG
ATTTGAGGTTGGTTTTAGGGTTGCTAGATTTAGCAAGTAAAAATAAGG
ATGGCCCCGTTAAATTTTAACTTAAAATTAACAAGTTTTTTGTTAATTTT
TTGTTTTTTGTCTCAGCATCAGTATATCCCATGCAATATTTGAGGTGT
GCTCATACTAAAATTATTTGTGTATCTGAAATTCAAATTAAACTGGGTG
```

-continued
TCTTTTTCTTTTCATCTGGCAACCCTACTAAGATCATAAACCCTTGGAA

ATCTGTGTGTGTGCGGGTGTGTGTGTGTGTGTGTGCAGGGGTGG

CAGAAGTACTGTGGGATGGGACAAAAAAAAAAAAAAAAAAAAAAAAA

AAAAAAA and homologues and fragments thereof.

It will be appreciated that the nucleotide sequence of SEQ I.D. No: 1 also includes control sequences, such as a polyadenylation sequence, providing for expression of the sequence in a host cell.

One particular DNA fragment according to the invention is the isolated human metallo-proteinase-encoding nucleotide sequence of SEQ I.D. No: 2:

SEQ I.D. No:2
ATGTTGCAAGGTCTCCTGCCAGTCAGTCTCCTCCTCTCTGTTGCAGT

AAGTGCTATAAAAGAACTCCCTGGGGTGAAGAAGTATGAAGTGGTTT

ATCCTATAAGACTTCATCCACTGCATAAAAGAGAGGCCAAAGAGCCA

GAGCAACAGGAACAATTTGAAACTGAATTAAAGTATAAAATGACAATT

AATGGAAAAATTGCAGTGCTTTATTTGAAAAAAAACAAGAACCTCCTT

GCACCAGGCTACACGGAAACATATTATAATTCCACTGGAAAGGAGAT

CACCACAAGCCCACAAATTATGGATGATTGTTATTATCAAGGACATAT

TCTTAATGAAAAGGTTTCTGACGCTAGCATCAGCACATGTAGGGGTC

TAAGGGGCTACTTCAGTCAGGGGGATCAAAGATACTTTATTGAACCTT

TAAGCCCCATACATCGGGATGGACAGGAGCATGCACTCTTCAAGTAT

AACCCTGATGAAAGAATTATGACAGCACCTGTGGGATGGATGGTGT

GTTGTGGGCCCACGATTTGCAGCAGAACATTGCCCTACCTGCCACCA

AACTAGTAAAATTGAAAGACAGGAAGGTTCAGGAACATGAGAAATAC

ATAGAATATTATTTGGTCCTGGATAATGGTGAGTTTAAAAGGTACAAT

GAGAATCAAGATGAGATCAGAAAGAGGGTATTTGAGATGGCTAATTA

TGTCAACATGCTTTATAAAAAGCTCAATACTCATGTGGCCTTAGTTGG

TATGGAAATCTGGACTGACAAGGATAAGATAAAGATAACCCCAAATG

CAAGCTTCACCTTGGAGAATTTTTCTAAATGGAGGGGAGTGTTCTCT

CAAGAAGAAAGCGTCATGATATTGCTCAGTTAATCACAGCAACAGAA

CTTGCTGGAACGACTGTGGGTCTTGCATTTATGTCTACAATGTGTTCT

CCTTATTCTGTTGGCGTTGTTCAGGACCACAGCGATAATCTTCTTAGA

GTTGCAGGGACAATGGCACATGAAATGGGCCACAACTTTGGAATGTT

TCATGACGACTATTCTTGCAAGTGTCCTTCTACAATATGTGTGATGGA

CAAAGCACTGAGCTTCTATATACCCACAGACTTCAGTTCCTGCAGCC

GTCTCAGCTATGACAAGTTTTTTGAAGATAAATTATCAAATTGCCTCTT

TAATGCTCCATTGCCTACAGATATCATATCCACTCCAATTTGTGGGAA

CCAGTTGGTGGAAATGGGAGAGGACTGTGATTGTGGGACATCTGAG

ACATGTAAAATCAAAGCAACTTTTCAATGTGCATTAGGAGAATGTTGT

GAAAAATGCCAATTTAAAAAGGCTGGGATGGTGTGCAGACCAGCAA

AGATGAGTGCGACCTGCCTGAAATGTGTAATGGTAAATCTGGTAATT

GTCCTGATGATAGATTCCAAGTCAATGGCTTCCCTTGCCATCACGGG

-continued
AAGGGCCACTGCTTGATGGGGACATGCCCCACACTGCAGGAGCAGT

GCACAGAGCTGTGGGGACCAGGTAGGAGGACAAATCCTTTCCCCTG

TGCATGTGCGAAGGAAAATCATTTCAGA and homologues and fragments thereof.

In the sequences herein standard one letter codes are used to represent nucleotides or amino acids as appropriate.

DNA according to the invention may be obtained using conventional molecular biology procedures, for example by probing a human genomic or cDNA library with one or more labelled oligonucleotide probes containing for example fifteen or more contiguous nucleotides designed using the nucleotide sequences described herein [see for example "Current Protocols in Molecular Biology", Ausubel, F M et al (eds), Greene Publishing Associates and Wiley-Interscience, New York (1987)].

Where the term homologue is used herein in relation to a particular nucleotide or amino acid sequence this is to be understood to represent a corresponding sequence in which one or more nucleotides or amino acids have been added, deleted, substituted or otherwise chemically modified, provided always that the homologue retains substantially the same catalytic properties as the particular sequence described. One particular type of homologue for example may be that in which one or more nucleotides have been substituted due to the degeneracy of the genetic code. Homologues may be obtained by standard molecular biology and/or chemistry techniques, e.g. by cDNA or gene cloning, or by use of oligonucleotide directed mutagenesis or oligonucleotide directed synthesis techniques or enzymatic cleavage or enzymatic filling in of gapped oligonucleotides (see for example Ausubel, F M ibid).

The DNA of SEQ I.D. No: 1 and SEQ I.D. No: 2 each codes for a human metalloproteinase. Thus, the DNA according to the invention or a fragment thereof may be used as a probe to screen an appropriate genomic or cDNA library in a process utilising standard hybridisation and/or PCR cloning techniques to obtain the gene or cDNA coding for a homologue or fragment of the metalloproteinase, or a related metalloproteinase from another species.

The DNA according to the invention may in turn be used to produce a metalloproteinase. In another aspect of the invention we therefore provide an isolated human metalloproteinase which has the amino acid sequence of SEQ I.D. No: 3:

SEQ I.D. No: 3
MLQGLLPVSLLLSVAVSAIKELPGVKKYEVVYPIRLHPLHKREAKEPEQQ

EQFETELKYKMTINGKIAVLYLKKNKNLLAPGYTETYYNSTGKEITTSPQI

MDDCYYQGHILNEKVSDASISTCRGLRGYFSQGDQRYFIEPLSPIHRDG

QEHALFKYNPDEKNYDSTCGMDGVLWAHDLQQNIALPATKLVKLKDRK

VQEHEKYIEYYLVLDNGEFKRYNENQDEIRKRVFEMANYVNMLYKKLNT

HVALVGMEIWTDKDKIKITPNASFTLENFSKWRGSVLSRRKRHDIAQLITA

TELAGTTVGLAFMSTMCSPYSVGVVQDHSDNLLRVAGTMAHEMGHNF

GMFHDDYSCKCPSTICVMDKALSFYIPTDFSSCSRLSYDKFFEDKLSNCL

FNAPLPTDIISTPICGNQLVEMGEDCDCGTSETCKIKATFQCALGECCEK

CQFKKAGMVCRPAKDECDLPEMCNGKSGNCPDDRFQVNGFPCHHGK

GHCLMGTCPTLQEQCTELWGPGRRTNPFPCACAKENHFR and homologues and fragments thereof.

The production of a protein according to the invention may be achieved using standard recombinant DNA techniques involving the expression of the metalloproteinase by a host cell. The isolated nucleic acids described herein may be for example introduced into any suitable expression vector by operatively linking the DNA to any necessary expression control elements therein and transforming any suitable procaryotic or eucaryotic host cell with the vector using well known procedures for example as described below in the production of antibodies. The invention is thus to be understood to extend to recombinant plasmids containing a gene of the invention or a nucleotide sequence of SEQ I.D. No: 1 or SEQ I.D. No: 2, to cells containing said recombinant plasmids and to a process for producing the protein according to the invention which comprises culturing said cells such that the desired protein is expressed and recovering the protein from the culture.

Thus in one example ,the nucleotide sequence of SEQ I.D. No: 1 without its 3' poly A tail, or SEQ I.D. No: 2 can be inserted downstream of the hCMV promoter in the pEE12 plasmid vector, and either transiently or stabily expressed in CHO-L761h or NSO mouse melanoma cells [Murphy et al., J. Biol. Chem., 267, 9612–9618 (1992)]. Expression of the enzyme according to the invention can be detected in serum free culture medium by its catalytic properties, for example as a gelatinolytic band of approximately 58000 kD from CHO cells, by analysis on a gelatin containing polyacrylamide gel [Murphy et al., Biochem. J., 283, 637–641 (1992)]. This assay can also be used during the subsequent isolation of the expressed enzyme from transfected cell conditioned medium. If the enzyme requires further activation, this may be achieved proteolytically through use of modest amounts of trypsin, furin, or other methods, in order to remove an approximately 180 amino acid N-terminal propeptide, as described for other metalloproteinases [Murphy et al., J. Biol. Chem., 267, 9612–9618 (1992); Crabbe et al., Biochemistry, 33, 14419–14425 (1994); Pei and Weiss, Nature, 375, 244–247 (1995); Will et al., J. Biol. Chem., 271, 17119–17123 (1996)].

It may be desirable to produce the catalytic domain of the protein according to the invention in isolation from the rest of the molecule. This may be achieved using the above standard recombinant DNA techniques except that in this instance the DNA sequence used is that encoding the amino acid sequence of SEQ I.D. No: 4:

---
SEQ I.D. No: 4

VQEHEKYIEYYLVLDNGEFKRYNENQDEIRKRVFEMANYVNMLYKKLNT

HVALVGMEIWTDKDKIKITPNASFTLENFSKWRGSVLSRRKRHDIAQLITA

TELAGTTVGLAFMSTMCSPYSVGVVQDHSDNLLRVAGTMAHEMGHNF

GMFHDDYSCKCPSTICVMDKALSFYIPTDFSSCSRLSYDKFFEDKLSNCL

FNAP

--- or a homologue thereof, and the invention extends to such isolated catalytic domains.

N or C-terminally extended versions of the sequence shown in SEQ I.D. No: 4 may be obtained by expression in procaryotic or eucaryotic cells as described above optionally attached to a peptide tag via which the protein may be affinity purified and identified. Examples of tags include the well known "His" or "Strep-tags". Further sequences that may be attached arise from expression in procaryotic cells and include the pelB or ompA leaders which when placed at the N-terminus help direct secretion to the E. coli periplasmic space [Schmidt and Skerra, J. Chromatography, 676, 337–345 (1994); Knauper et al., J. Biol. Chem., 271, 17124–17131 (1996)].

The nucleotide sequences according to the invention may also be of use in diagnosis, for example to determine enzyme deficiency in a human subject, by for example direct DNA sequence comparison or DNA/RNA hybridisation assays; or in therapy, for example where it is desired to modify the production of the metalloproteinase in vivo, and the invention extends to such uses.

Knowledge of the gene according to the invention also provides the ability to regulate its activity in vivo by for example the use of antisense DNA or RNA. Thus, according to a further aspect of the invention we provide an antisense DNA or an antisense RNA of a gene coding for a human metalloproteinase, said gene containing the nucleotide sequence of SEQ I.D. No: 1 or SEQ I.D. No: 2.

The antisense DNA or RNA will correspond to the metalloproteinase gene or a fragment thereof, for example a fragment based on the nucleotide sequence of SEQ I.D. No: 1 or SEQ I.D. No: 2. The antisense DNA or RNA can be produced using conventional means, by standard molecular biology and/or by chemical synthesis as described above. If desired, the antisense DNA and antisense RNA may be chemically modified so as to prevent degradation in vivo or to facilitate passage through a cell membrane, and/or a substance capable of inactivating mRNA, for example ribosyme, may be linked thereto, and the invention extends to such constructs.

The antisense DNA or antisense RNA may be of use in the treatment of diseases or disorders in humans in which the over- or unregulated production of the metalloproteinase has been implicated. Such diseases or disorders may include those described under the general headings of infectious diseases, e.g. HIV infection; inflammatory disease/autoimmunity e.g. rheumatoid arthritis, inflammatory bowel disease; osteoarthritis; cancer; allergic/atopic diseases e.g. asthma, eczema; cardiovascular disease e.g. myocardial infarction, congestive heart failure; systemic inflammatory response syndrome e.g. sepsis syndrome; reperfusion injury; malignancy; cachexia; congenital e.g. cystic fibrosis, sickle cell anaemia; dermatologic, e.g. psoriasis, alopecia; neurologic, e.g. multiple sclerosis, migraine headache; renal e.g. uraemia, nephrotic syndrome; obstetric/gynecologic e.g. premature labour, miscarriage, genitourinary prolapse, urinary incontinence, contraception, infertility; transplants e.g. organ transplant rejection, graft-versus-host disease; metabolic/idiopathic disease e.g. diabetes; disorders of the bone such as osteoporosis; and toxicity e.g. due to chemotherapy, cytokine therapy, and anti-CD3 therapy.

The metalloproteinase according to the invention and homologues or fragments thereof may be used to generate substances which selectively bind to the proteins and in so doing regulate the activity of the enzymes. Such substances include, for example, antibodies, and the invention extends in particular to an antibody which is capable of recognising one or more epitopes on a metalloproteinase containing the amino acid sequence of SEQ I.D. No: 3 or a homologue or fragment thereof. In particular the antibody may be a neutralising antibody.

As used herein the term antibody is to be understood to mean a whole antibody or a fragment thereof, for example a F(ab)$_2$, Fab, Fv, $V_H$ or $V_K$ fragment, a single-chain antibody, a multimeric monospecific antibody or fragment thereof, or a bi- or multispecific antibody or fragment thereof.

The antibody according to the invention may be a polyclonal or, especially, a monoclonal antibody. The antibody may belong to any immunoglobulin class, and may be for example an IgG, for example IgG$_1$, IgG$_2$, IgG$_3$ IgG$_4$, IgE, IgM or IgA antibody. It may be of animal, for example mammalian origin, and may be for example a murine, rat or human antibody. Alternatively, the antibody may be a chimeric antibody. The term chimeric antibody is used herein to mean any antibody containing portions derived from different animal species. Particular examples include those antibodies having a variable region derived from a murine or other antibody constant region, and those antibodies in which one or more CDR sequences and optionally one or more variable region framework amino acids are derived from a murine or other antibody and the remaining portions of the variable and the constant regions are derived from a human immunoglobulin.

Antibodies according to the invention may be prepared by conventional immunisation and recombinant DNA techniques. Thus, for example polyclonal antibodies may be obtained from the sera of animals immunised with a metalloproteinase according to the invention or a homologue or fragment thereof. Any suitable host, for example BALB/c mice where it is desired to obtain a mouse polyclonal antibody, may be injected with the immunogen, the serum collected and the antibody recovered therefrom. Monoclonal antibodies may be obtained from hybridomas derived from the spleen cells of an animal immunised as just discussed and fused to an appropriate "immortal" B-tumour cell. In each instance, the antibody may be recovered from either the serum or the hybridoma by making use of standard purification and or concentration techniques, for example by chromatography, using for example Protein A or by other affinity chromatography employing a metalloproteinase of the invention or a homologue or fragment thereof.

Once a cell line, for example a hybridoma, expressing an antibody according to the invention has been obtained it is possible to clone therefrom the cDNA and to identify the variable region genes encoding the desired antibody, including the sequences encoding the CDRs. From here, other chimeric antibodies according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming an appropriate cell line, e.g. a non-producing myeloma cell line, such as a mouse NSO line, in which production of the antibody will occur. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al [Molecular Cloning, Cold Spring Harbor Laboratory, New York, 1989]; DNA sequencing can be performed as described in Sanger et al [PNAS 74, 5463, (1977)] and the Amersham International plc sequencing handbook; and site directed mutagenesis can be carried out according to the method of Kramer et al [Nucl. Acids Res. 12, 9441, (1984)] and the Anglian Biotechnology Ltd handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews [ed. Tombs, M P, 10, Chapter 1, 1992, Intercept, Andover, UK] and in International Patent Specification No. WO 91/09967.

Antibodies and other selective binding agents according to the invention may be of use in therapy, either alone or as a delivery agent, for the delivery of a drug, prodrug, radiometal or radioisotope, for example in the treatment of diseases such as those described above in humans and/or other animals, or may find a use as purification agents in the preparation of the human metalloproteinase or homologues or fragments thereof.

In a further use according to the invention, selective binding agents of the invention, such as antibodies, may form the basis of a diagnostic assay to detect the presence or absence in a biological sample (e.g. serum, synovial fluid or a tissue extract) of a metalloproteinase as described herein. Thus for example the binding agent may be brought into contact with a sample of serum, synovial fluid or tissue under conditions in which a complex is formed between the binding agent and target metalloproteinase. Qualitative and/or quantitative detection of the complex can then be used to determine the presence or absence of the metalloproteinase and in particular whether the enzyme is present in an abnormal quantity associated for example with a particular disease state.

The metalloproteinases according to the invention may in particular be used to screen for compounds which regulate the activity of the enzymes and the invention extends to such a screen and to the use of compounds obtainable therefrom to regulate metalloproteinases in vivo.

Thus according to a further aspect of the invention we provide a process for obtaining a compound capable of regulating the action of a human metalloproteinase in vivo which comprises subjecting one or more test compounds to a screen comprising (A) a metalloproteinase having the amino acid sequence of SEQ I.D. No: 3 or a homologue or fragment thereof, or (B) a host cell transformed to be capable of expressing a nucleotide sequence of SEQ I.D. No: 1 or SEQ I.D. No: 2 or a homologue or fragment thereof.

The screen according the invention may be operated using conventional procedures, for example by bringing the test compound or compounds to be screened and an appropriate substrate into contact with the metalloproteinase or a cell capable of producing it and determining affinity for the protein in accordance with standard practice.

Any compound obtainable in this way may have a potential use in the treatment in humans and/or other animals of one or more of the above mentioned diseases. The invention thus extends to a compound selected through its ability to regulate the activity of a metalloproteinase in vivo as primarily determined in a screening assay utilising a metalloproteinase having an amino acid sequence of SEQ I.D. No: 3 or a homologue or fragment thereof or a gene coding therefor, for use in the treatment of a disease in which the over- or under-activity or unregulated activity of the metalloproteinase is implicated.

We claim:

1. An isolated polynucleotide comprising a member selected from the group consisting of:
   (a) a polynucleotide comprising at most 2056 nucleotides encoding the protein set forth in SEQ ID NO:3;
   (b) a polynucleotide capable of selectively hybridizing to SEQ ID NO:1, nuclotides 1–2225, or SEQ ID NO:2; and
   (c) a polynucleotide comprising a nucleotide sequence fully complementary to the polynucleotide of (a) or (b).

2. The isolated polynucleotide of claim 1 wherein said polynucleotide consists of SEQ ID NO 1 or SEQ ID NO:2.

3. The isolated polynucleotide of claim 1 wherein said polynucleotide is an antisense DNA or an antisense RNA.

4. An isolated human metalloproteinase comprising the amino acid sequence of SEQ ID NO:3.

5. An antibody which is capable of recognizing one or more epitopes of a metalloproteinase according to claim 4.

6. A process for obtaining a compound capable of regulating the action of a human metalloproteinase in vivo which comprises subjecting one or more compounds to a screen comprising a metalloproteinase according to claim 4.

7. A process for obtaining a compound capable of regulating a human metalloproteinase in vivo which comprises subjecting one or more test compounds to a screen comprising a host cell transformed to be capable of expressing a nucleotide sequence according to claims 1 or 2.

8. An isolated human metalloproteinase comprising the amino acid sequence of SEQ ID NO:4.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 2056 base pairs
       (B) TYPE: nucleic acid
       (C) STRANDEDNESS: single
       (D) TOPOLOGY: linear (xi) SEQUENCE DESCRIPTION: SEQ ID NO:1:

```
GAGAAGAGCA GACACCGTGC TCCTGGAATC ACCCAGCATG TTGCAAGGTC TCCTGCCAGT      60

CAGTCTCCTC CTCTCTGTTG CAGTAAGTGC TATAAAAGAA CTCCCTGGGG TGAAGAAGTA     120

TGAAGTGGTT TATCCTATAA GACTTCATCC ACTGCATAAA AGAGAGGCCA AAGAGCCAGA     180

GCAACAGGAA CAATTTGAAA CTGAATTAAA GTATAAAATG ACAATTAATG GAAAAATTGC     240

AGTGCTTTAT TTGAAAAAAA ACAAGAACCT CCTTGCACCA GGCTACACGG AAACATATTA     300

TAATTCCACT GGAAAGGAGA TCACCACAAG CCCACAAATT ATGGATGATT GTTATTATCA     360

AGGACATATT CTTAATGAAA AGGTTTCTGA CGCTAGCATC AGCACATGTA GGGGTCTAAG     420

GGGCTACTTC AGTCAGGGGG ATCAAAGATA CTTTATTGAA CCTTTAAGCC CCATACATCG     480

GGATGGACAG GAGCATGCAC TCTTCAAGTA TAACCCTGAT GAAAGAATT ATGACAGCAC      540

CTGTGGGATG GATGGTGTGT TGTGGGCCCA CGATTTGCAG CAGAACATTG CCCTACCTGC     600

CACCAAACTA GTAAAATTGA AGACAGGAA GGTTCAGGAA CATGAGAAAT ACATAGAATA      660

TTATTTGGTC CTGGATAATG GTGAGTTTAA AAGGTACAAT GAGAATCAAG ATGAGATCAG     720

AAAGAGGGTA TTTGAGATGG CTAATTATGT CAACATGCTT TATAAAAAGC TCAATACTCA     780

TGTGGCCTTA GTTGGTATGG AAATCTGGAC TGACAAGGAT AAGATAAAGA TAACCCCAAA     840

TGCAAGCTTC ACCTTGGAGA ATTTTTCTAA ATGGAGGGGG AGTGTTCTCT CAAGAAGAAA     900

GCGTCATGAT ATTGCTCAGT TAATCACAGC AACAGAACTT GCTGGAACGA CTGTGGGTCT     960

TGCATTTATG TCTACAATGT GTTCTCCTTA TTCTGTTGGC GTTGTTCAGG ACCACAGCGA    1020

TAATCTTCTT AGAGTTGCAG GGACAATGGC ACATGAAATG GGCCACAACT TGGAATGTT    1080

TCATGACGAC TATTCTTGCA AGTGTCCTTC TACAATATGT GTGATGGACA AAGCACTGAG    1140

CTTCTATATA CCCACAGACT TCAGTTCCTG CAGCCGTCTC AGCTATGACA AGTTTTTTGA    1200

AGATAAATTA TCAAATTGCC TCTTTAATGC TCCATTGCCT ACAGATATCA TATCCACTCC    1260

AATTTGTGGG AACCAGTTGG TGGAAATGGG AGAGGACTGT GATTGTGGGA CATCTGAGAC    1320

ATGTAAAATC AAAGCAACTT TTCAATGTGC ATTAGGAGAA TGTTGTGAAA AATGCCAATT    1380

TAAAAAGGCT GGGATGGTGT GCAGACCAGC AAAAGATGAG TGCGACCTGC CTGAAATGTG    1440

TAATGGTAAA TCTGGTAATT GTCCTGATGA TAGATTCCAA GTCAATGGCT TCCCTTGCCA    1500

TCACGGGAAG GGCCACTGCT TGATGGGGAC ATGCCCCACA CTGCAGGAGC AGTGCACAGA    1560

GCTGTGGGGA CCAGGTAGGA GGACAAATCC TTTCCCCTGT GCATGTGCGA AGGAAAATCA    1620

TTTCAGATGA CAGTGTTTAA CCATGGTCAA AGGACCATTG TGTCCTATCC TTCTTAGAAG    1680

CTTCGAACTC AAAATCATGG AAAGGTTTTA AGATTTGAGG TTGGTTTTAG GGTTGCTAGA    1740

TTTAGCAAGT AAAAATAAGG ATGGCCCCGT TAAATTTTAA CTTAAAATTA ACAAGTTTTT    1800

TGTTAATTTT TTGTTTTTTG TCTCAGCATC AGTATATCCC ATGCAATATT TGAGGTGTGC    1860
```

```
TCATACTAAA ATTATTTGTG TATCTGAAAT TCAAATTAAA CTGGGTGTCT TTTTCTTTTC    1920

ATCTGGCAAC CCTACTAAGA TCATAAACCC TTGGAAATCT GTGTGTGTGC GGGTGTGTGT    1980

GTGTGTGTGT GTGCAGGGGT GGCAGAAGTA CTGTGGGATG GACAAAAAA AAAAAAAAAA    2040

AAAAAAAAAA AAAAAA                                                    2056
```

(2) INFORMATION FOR SEQ ID NO:2:

(i) SEQUENCE CHARACTERISTICS:
        (A) LENGTH: 1590 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
ATGTTGCAAG GTCTCCTGCC AGTCAGTCTC CTCCTCTCTG TTGCAGTAAG TGCTATAAAA      60

GAACTCCCTG GGGTGAAGAA GTATGAAGTG GTTTATCCTA TAAGACTTCA TCCACTGCAT     120

AAAGAGAGG CCAAAGAGCC AGAGCAACAG GAACAATTTG AAACTGAATT AAAGTATAAA      180

ATGACAATTA ATGGAAAAAT TGCAGTGCTT TATTTGAAAA AAAACAAGAA CCTCCTTGCA     240

CCAGGCTACA CGGAAACATA TTATAATTCC ACTGGAAAGG AGATCACCAC AAGCCCACAA     300

ATTATGGATG ATTGTTATTA TCAAGGACAT ATTCTTAATG AAAAGGTTTC TGACGCTAGC     360

ATCAGCACAT GTAGGGGTCT AAGGGGCTAC TTCAGTCAGG GGGATCAAAG ATACTTTATT     420

GAACCTTTAA GCCCCATACA TCGGGATGGA CAGGAGCATG CACTCTTCAA GTATAACCCT     480

GATGAAAAGA ATTATGACAG CACCTGTGGG ATGGATGGTG TGTTGTGGGC CCACGATTTG     540

CAGCAGAACA TTGCCCTACC TGCCACCAAA CTAGTAAAAT TGAAAGACAG GAAGGTTCAG     600

GAACATGAGA AATACATAGA ATATTATTTG GTCCTGGATA ATGGTGAGTT TAAAAGGTAC     660

AATGAGAATC AAGATGAGAT CAGAAAGAGG GTATTTGAGA TGGCTAATTA TGTCAACATG     720

CTTTATAAAA AGCTCAATAC TCATGTGGCC TTAGTTGGTA TGGAAATCTG GACTGACAAG     780

GATAAGATAA AGATAACCCC AAATGCAAGC TTCACCTTGG AGAATTTTTC TAAATGGAGG     840

GGGAGTGTTC TCTCAAGAAG AAAGCGTCAT GATATTGCTC AGTTAATCAC AGCAACAGAA     900

CTTGCTGGAA CGACTGTGGG TCTTGCATTT ATGTCTACAA TGTGTTCTCC TTATTCTGTT     960

GGCGTTGTTC AGGACCACAG CGATAATCTT CTTAGAGTTG CAGGGACAAT GGCACATGAA    1020

ATGGGCCACA ACTTTGGAAT GTTTCATGAC GACTATTCTT GCAAGTGTCC TTCTACAATA    1080

TGTGTGATGG ACAAAGCACT GAGCTTCTAT ATACCCACAG ACTTCAGTTC CTGCAGCCGT    1140

CTCAGCTATG ACAAGTTTTT TGAAGATAAA TTATCAAATT GCCTCTTTAA TGCTCCATTG    1200

CCTACAGATA TCATATCCAC TCCAATTTGT GGGAACCAGT TGGTGGAAAT GGGAGAGGAC    1260

TGTGATTGTG GACATCTGA GACATGTAAA ATCAAAGCAA CTTTTCAATG TGCATTAGGA    1320

GAATGTTGTG AAAAATGCCA ATTTAAAAAG GCTGGGATGG TGTGCAGACC AGCAAAAGAT    1380

GAGTGCGACC TGCCTGAAAT GTGTAATGGT AAATCTGGTA ATTGTCCTGA TGATAGATTC    1440

CAAGTCAATG GCTTCCCTTG CCATCACGGG AAGGGCCACT GCTTGATGGG GACATGCCCC    1500

ACACTGCAGG AGCAGTGCAC AGAGCTGTGG GGACCAGGTA GGAGGACAAA TCCTTTCCCC    1560

TGTGCATGTG CGAAGGAAAA TCATTTCAGA                                    1590
```

(2) INFORMATION FOR SEQ ID NO:3:

(i) SEQUENCE CHARACTERISTICS:
        (A) LENGTH: 529 amino acids (B) TYPE: amino acid
(C) STRANDEDNESS: single
(D) TOPOLOGY: linear (ii) MOLECULE TYPE: None (xi) SEQUENCE DESCRIPTION: SEQ ID NO:3:

```
Met Leu Gln Gly Leu Leu Pro Val Ser Leu Leu Ser Val Ala Val
 1               5                  10                  15

Ser Ala Ile Lys Glu Leu Pro Gly Val Lys Tyr Glu Val Val Tyr
             20                  25                  30

Pro Ile Arg Leu His Pro Leu His Lys Arg Glu Ala Lys Glu Pro Glu
         35                  40                  45

Gln Gln Glu Gln Phe Glu Thr Glu Leu Lys Tyr Lys Met Thr Ile Asn
 50                  55                  60

Gly Lys Ile Ala Val Leu Tyr Leu Lys Lys Asn Lys Asn Leu Leu Ala
 65              70                  75                      80

Pro Gly Tyr Thr Glu Thr Tyr Tyr Asn Ser Thr Gly Lys Glu Ile Thr
             85                  90                  95

Thr Ser Pro Gln Ile Met Asp Asp Cys Tyr Tyr Gln Gly His Ile Leu
            100                 105                 110

Asn Glu Lys Val Ser Asp Ala Ser Ile Ser Thr Cys Arg Gly Leu Arg
            115                 120                 125

Gly Tyr Phe Ser Gln Gly Asp Gln Arg Tyr Phe Ile Glu Pro Leu Ser
130                 135                 140

Pro Ile His Arg Asp Gly Gln Glu His Ala Leu Phe Lys Tyr Asn Pro
145                 150                 155                 160

Asp Glu Lys Asn Tyr Asp Ser Thr Cys Gly Met Asp Gly Val Leu Trp
                165                 170                 175

Ala His Asp Leu Gln Gln Asn Ile Ala Leu Pro Ala Thr Lys Leu Val
            180                 185                 190

Lys Leu Lys Asp Arg Lys Val Gln Glu His Glu Lys Tyr Ile Glu Tyr
            195                 200                 205

Tyr Leu Val Leu Asp Asn Gly Glu Phe Lys Arg Tyr Asn Glu Asn Gln
210                 215                 220

Asp Glu Ile Arg Lys Arg Val Phe Glu Met Ala Asn Tyr Val Asn Met
225                 230                 235                 240

Leu Tyr Lys Lys Leu Asn Thr His Val Ala Leu Val Gly Met Glu Ile
                245                 250                 255

Trp Thr Asp Lys Asp Lys Ile Lys Ile Thr Pro Asn Ala Ser Phe Thr
            260                 265                 270

Leu Glu Asn Phe Ser Lys Trp Arg Gly Ser Val Leu Ser Arg Arg Lys
            275                 280                 285

Arg His Asp Ile Ala Gln Leu Ile Thr Ala Thr Glu Leu Ala Gly Thr
290                 295                 300

Thr Val Gly Leu Ala Phe Met Ser Thr Met Cys Ser Pro Tyr Ser Val
305                 310                 315                 320

Gly Val Val Gln Asp His Ser Asp Asn Leu Leu Arg Val Ala Gly Thr
                325                 330                 335

Met Ala His Glu Met Gly His Asn Phe Gly Met Phe His Asp Asp Tyr
            340                 345                 350

Ser Cys Lys Cys Pro Ser Thr Ile Cys Val Met Asp Lys Ala Leu Ser
            355                 360                 365

Phe Tyr Ile Pro Thr Asp Phe Ser Cys Ser Arg Leu Ser Tyr Asp
370                 375                 380
```

```
Lys Phe Phe Glu Asp Lys Leu Ser Asn Cys Leu Phe Asn Ala Pro Leu
385                 390                 395                 400

Pro Thr Asp Ile Ile Ser Thr Pro Ile Cys Gly Asn Gln Leu Val Glu
            405                 410                 415

Met Gly Glu Asp Cys Asp Cys Gly Thr Ser Glu Thr Cys Lys Ile Lys
            420                 425                 430

Ala Thr Phe Gln Cys Ala Leu Gly Glu Cys Cys Glu Lys Cys Gln Phe
        435                 440                 445

Lys Lys Ala Gly Met Val Cys Arg Pro Ala Lys Asp Glu Cys Asp Leu
    450                 455                 460

Pro Glu Met Cys Asn Gly Lys Ser Gly Asn Cys Pro Asp Asp Arg Phe
465                 470                 475                 480

Gln Val Asn Gly Phe Pro Cys His Gly Lys Gly His Cys Leu Met Gly
                485                 490                 495

Thr Cys Pro Thr Leu Gln Glu Gln Cys Thr Glu Leu Trp Gly Pro Gly
            500                 505                 510

Arg Arg Thr Asn Pro Phe Pro Cys Ala Cys Ala Lys Glu Asn His Phe
        515                 520                 525

Arg (2) INFORMATION FOR SEQ ID NO:4:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

Val Gln Glu His Glu Lys Tyr Ile Glu Tyr Tyr Leu Val Leu Asp Asn
1               5                   10                  15

Glu Phe Lys Arg Tyr Asn Glu Asn Gln Asp Glu Ile Arg Lys Arg Val
            20                  25                  30

Phe Glu Met Ala Asn Tyr Val Asn Met Leu Tyr Lys Lys Leu Asn Thr
        35                  40                  45

His Val Ala Leu Val Gly Met Glu Ile Trp Thr Asp Lys Asp Lys Ile
    50                  55                  60

Lys Ile Thr Pro Asn Ala Ser Phe Thr Leu Glu Asn Phe Ser Lys Trp
65                  70                  75                  80

Arg Gly Ser Val Leu Ser Arg Arg Lys Arg His Asp Ile Ala Gln Leu
            85                  90                  95

Ile Thr Ala Thr Glu Leu Ala Gly Thr Thr Val Gly Leu Ala Phe Met
            100                 105                 110

Ser Thr Met Cys Ser Pro Tyr Ser Val Gly Val Gln Asp His Ser
        115                 120                 125

Asp Asn Leu Leu Arg Val Ala Gly Thr Met Ala His Glu Met Gly His
    130                 135                 140

Asn Phe Gly Met Phe His Asp Asp Tyr Ser Cys Lys Cys Pro Ser Thr
145                 150                 155                 160

Ile Cys Val Met Asp Lys Ala Leu Ser Phe Tyr Ile Pro Thr Asp Phe
            165                 170                 175

Ser Ser Cys Ser Arg Leu Ser Tyr Asp Lys Phe Phe Glu Asp Lys Leu
            180                 185                 190
```

-continued

```
Ser Asn Cys Leu Phe Asn Ala Pro
    195                 200
```